(12) United States Patent
Li et al.

(10) Patent No.: US 8,772,483 B2
(45) Date of Patent: Jul. 8, 2014

(54) SOLID FORMS OF (S)-2-AMINO-3-(4-(2-AMINO-6-((R)-1-(4-CHLORO-2-(3-METHYL-1H-PYRAZOL-1-YL)PHENYL)-2,2,2-TRIFLUOROETHOXY)PYRIMIDIN-4-YL)PHENYL)PROPANOIC ACID

(75) Inventors: Qun Li, Newark, DE (US); Weifeng Hu, Shanghai (CN); Xiaogen Yang, Shanghai (CN); Jiangqiong Zhao, Shanghai (CN); Matthew Mangzhu Zhao, Edison, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 250 days.

(21) Appl. No.: 13/288,366

(22) Filed: Nov. 3, 2011

(65) Prior Publication Data

US 2012/0122904 A1 May 17, 2012

Related U.S. Application Data

(60) Provisional application No. 61/410,421, filed on Nov. 5, 2010.

(51) Int. Cl.
C07D 403/12 (2006.01)
A61K 31/506 (2006.01)
A61P 35/00 (2006.01)

(52) U.S. Cl.
CPC ............. C07D 403/12 (2013.01); *A61K 31/506* (2013.01)
USPC .......................................... 544/320; 514/269

(58) Field of Classification Search
CPC .............................. C07D 403/12; A61K 31/506
USPC ........................................... 544/320; 514/269
See application file for complete search history.

(56) References Cited

U.S. PATENT DOCUMENTS

| | | | |
|---|---|---|---|
| 7,553,840 B2 * | 6/2009 | Devasagayaraj et al. ..... | 514/269 |
| 7,709,493 B2 * | 5/2010 | Devasagayaraj et al. ..... | 514/269 |
| 7,723,345 B2 * | 5/2010 | Devasagayaraj et al. ..... | 514/269 |
| 7,855,291 B2 | 12/2010 | Burgoon | |
| 7,897,763 B2 | 3/2011 | Burgoon | |
| 7,968,559 B2 * | 6/2011 | Devasagayaraj et al. ..... | 514/269 |
| 7,968,729 B2 | 6/2011 | Bednarz | |
| 8,063,057 B2 * | 11/2011 | Devasagayaraj et al. ..... | 514/272 |
| 8,450,532 B2 | 5/2013 | Burgoon | |
| 8,575,362 B2 | 11/2013 | Bednarz | |

OTHER PUBLICATIONS

Freshney et al., Culture of Animal Cells, A Manual of Basic Technique, Alan R. Liss, Inc., 1983, New York, p. 4.*
Dermer et al., Bio/Technology, 1994, 12:320.*
Turner et al., Pharmacology & Therapeutics, 109, 325-338, 2006.*
Shishkina et al., Neuroscience, 150, 404-412, 2007.*
Bastin, R.J. et al., *Org. Process. Res. Dev.* 4(5):427-435 (2000).
Caira, M.R., *Topics Curr. Chem*. 198:163-208 (1998).
Hilfiker R., "Polymorphism in the Pharmaceutical Industry" 1-19 (2006).
International Search Report for Corresponding Patent Application No. PCT/US2011/059107, dated Jan. 11, 2012.

\* cited by examiner

*Primary Examiner* — Venkataraman Balasubramanian
(74) *Attorney, Agent, or Firm* — Max Bachrach

(57) ABSTRACT

Solid forms of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid and salts thereof are disclosed. Pharmaceutical dosage forms and methods of their use are also disclosed.

12 Claims, 1 Drawing Sheet

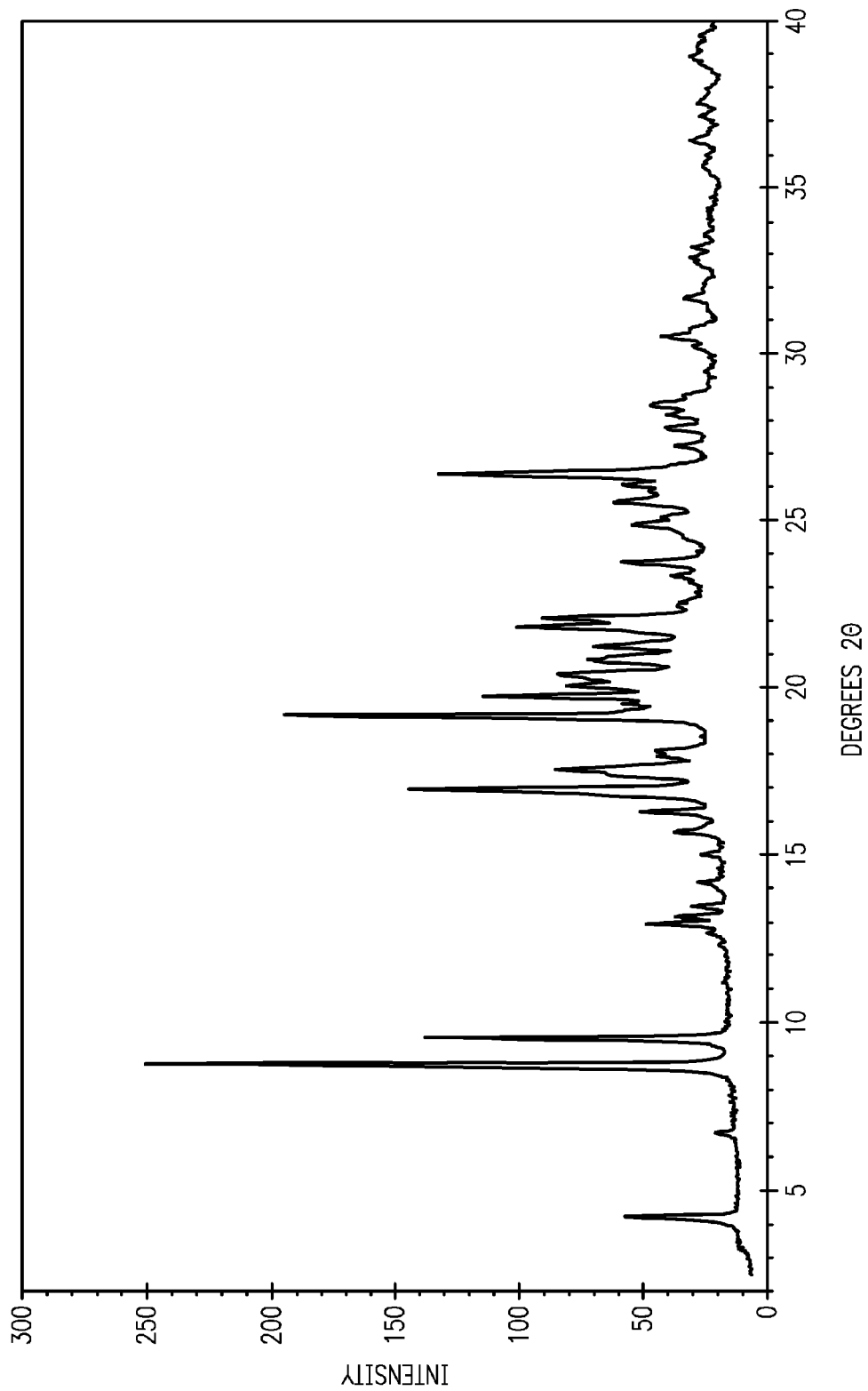

SOLID FORMS OF (S)-2-AMINO-3-(4-(2-AMINO-6-((R)-1-(4-CHLORO-2-(3-METHYL-1H-PYRAZOL-1-YL)PHENYL)-2,2,2-TRIFLUOROETHOXY)PYRIMIDIN-4-YL)PHENYL)PROPANOIC ACID

This application claims priority to U.S. provisional patent application No. 61/410,421, filed Nov. 5, 2010, the entirety of which is incorporated herein by reference.

1. FIELD OF THE INVENTION

This invention relates to solid forms of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid and salts thereof, compositions comprising them, and methods of their use.

2. BACKGROUND OF THE INVENTION

Different solid forms of the same compound can have substantially different properties. For example, the amorphous form of a drug may exhibit different dissolution characteristics and different bioavailability patterns than its crystalline form(s), properties which can affect how the drug must be administered to achieve optimal effect. Amorphous and crystalline forms of a drug may also have different handling properties (e.g., flowability, compressibility), dissolution rates, solubilities and stabilities, all of which can affect the manufacture of dosage forms. Consequently, access to multiple forms of a drug is desirable for a variety of reasons. Moreover, regulatory authorities (e.g., the U.S. Food and Drug Administration) may require the identification of all solid forms of a new drug substance before approving products containing it. A. Goho, *Science News* 166(8):122-123 (2004).

Compounds may exist in one or more crystalline forms, but the existence and characteristics of those forms cannot be predicted with any certainty. And even after one polymorph has been identified, the existence and characteristics of other forms can only be determined by additional experimentation. Id.

3. SUMMARY OF THE INVENTION

This invention is directed, in part, to solid forms of the tryptophan hydroxylase inhibitor (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid and pharmaceutically acceptable salts thereof. Particular solid forms are crystalline.

One embodiment of the invention encompasses pharmaceutical compositions comprising the solid forms described herein. Another encompasses methods of their use.

4. BRIEF DESCRIPTION OF THE FIGURES

Certain aspects of the invention may be understood with reference to the attached FIGURE.

FIG. 1 is an X-ray diffraction pattern of a crystalline solid form of anhydrous (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid besylate, referred to herein as Form C. The diffractogram was obtained using a Bruker D8 Advance system (Cu Kα radiation).

5. DETAILED DESCRIPTION OF THE INVENTION

This invention is directed, in part, to solid (e.g., crystalline) forms of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid and salts (e.g., pharmaceutically acceptable salts) thereof. The compound is an inhibitor of tryptophan hydroxylase, and may be used to treat a wide range of diseases and disorders mediated by serotonin. See, e.g., U.S. Pat. Nos. 7,553,840 and 7,709,493.

This invention is also directed to dosage forms comprising solid forms of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid, and to methods of their use.

5.1. Definitions

Unless otherwise indicated, the phrases "disease or disorder mediated by peripheral serotonin" and "disease and disorder mediated by peripheral serotonin" mean a disease and/or disorder having one or more symptoms, the severity of which is or are affected by peripheral serotonin levels.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or to prevent its recurrence. A prophylactically effective amount of a compound means an amount of therapeutic agent, alone or in combination with other agents, which provides a prophylactic benefit in the prevention of the disease or condition. The term "prophylactically effective amount" can encompass an amount that improves overall prophylaxis or enhances the prophylactic efficacy of another prophylactic agent.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder or one or more of its symptoms, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should also be noted that any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. Structures that represent compounds with one or more chiral centers, but which do not indicate stereochemistry (e.g., with bolded or dashed lines), encompasses pure stereoisomers and mixtures (e.g., racemic mixtures) thereof. Similarly, names of compounds having one or more chiral centers that do not specify the stereochemistry of those centers encompass pure stereoisomers and mixtures thereof.

5.2. Solid Forms

This invention is directed to solid forms of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid:

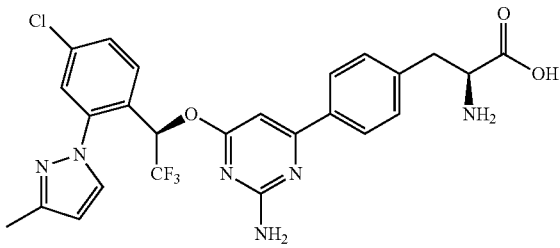 [SMILES: Cc1ccn(-c2cc(Cl)ccc2[C@@H](Oc2cc(-c3ccc(C[C@H](N)C(=O)O)cc3)nc(N)n2)C(F)(F)F)n1]

and salts thereof. Particular forms are crystalline. Also encompassed by the invention are crystalline salts of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid, including besylate, choline, dibesylate, edisilate, esylate, isopropyl sulfate, nicotinate, succinate, and thiocyanate salts.

One embodiment of the invention encompasses crystalline (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid. A particular form has a differential scanning calorimetry (DSC) peak at about 126° C. When used herein in connection with DSC data, the term "about" means±3.0° C.

Another embodiment of the invention encompasses crystalline besylate salts of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid.

A particular form of this compound ("Form A") is anhydrous (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid besylate having a melting point of about 234° C. as determined by DSC (onset temperature). A specific form has a DSC peak at about 238° C. A specific form provides an X-ray diffraction (XRPD) pattern with peaks at one or more of about 9.2, 15.9, 16.8, 18.4, 19.8, and/or 20.8 degrees 2θ. When used herein in connection with XRPD data, the term "about" means±0.3 degrees. One embodiment of the invention encompasses Form A having an XRPD pattern with peaks at about 15.9, 16.8, and 18.4 degrees 2θ.

Another form ("Form B") is (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid besylate monohydrate. A particular form has a melting point of about 218° C. (DSC onset temperature). A specific form has a DSC peak at about 230° C. A specific form provides an XRPD pattern with peaks at one or more of about 8.7, 9.1, 13.4, 18.3, and/or 20.2 degrees 2θ. Thus, one embodiment of the invention encompasses Form B having an XRPD pattern with peaks at about 8.7, 9.1, and 13.4 degrees 2θ.

Another form ("Form C") is anhydrous (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid besylate having a melting point of about 228° C. (DSC onset temperature). A specific form has a DSC peak at about 233° C. A specific form provides an XRPD pattern with peaks at one or more of about 8.7, 9.5, 16.9, 17.5, 19.1, 19.7, 20.1, 20.4, 21.8, 22.1, and/or 26.4 degrees 2θ. Thus, one embodiment of the invention encompasses Form C having an XRPD pattern with peaks at about 8.7 and 9.5 degrees 2θ. Another embodiment encompasses Form C having an XRPD pattern with peaks at about 8.7, 9.5, and 19.1 degrees 2θ. Another embodiment encompasses Form C having an XRPD pattern with peaks at about 16.9, 19.1, and 26.4 degrees 2θ. As those skilled in the art are well aware, the relative intensities of peaks in a XRPD pattern of a crystalline material can vary depending on how the sample is prepared and how the data is collected. With this in mind, an example of a XRPD pattern of this crystalline form is provided in FIG. 1.

Another form ("Form D") is anhydrous (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid besylate having a melting point of about 234° C. (DSC onset temperature). A specific form has a DSC peak at about 238° C. A specific form provides an XRPD pattern with peaks at one or more of about 7.6, 8.6, 12.9, 15.0, 15.3, 17.3, 19.2, 19.5, 20.2, and/or 23.1 degrees 2θ. Thus, one embodiment of the invention encompasses Form D having an XRPD pattern with peaks at about 8.6, 12.9, and 15.0 degrees 2θ. Another embodiment encompasses Form D having an XRPD pattern with peaks at about 15.3, 17.3, and 19.2 degrees 2θ. Another embodiment encompasses Form D having an XRPD pattern with peaks at about, 19.2, 19.5, and 20.2 degrees 2θ.

Another embodiment of the invention encompasses crystalline dibesylate salts of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid. A particular form has a melting point of about 223° C. (DSC onset temperature). A specific form has a DSC peak at about 227° C. A specific form provides an XRPD pattern with peaks at one or more of about 4.7, 13.8, 18.3, 20.0, 20.3, 21.6, and/or 21.9 degrees 2θ. Thus, one embodiment of the invention encompasses a crystalline dibesylate salt of the compound having an XRPD pattern with peaks at about 18.3, 20.0, and 20.3 degrees 2θ.

Another embodiment of the invention encompasses crystalline edisilate salts of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid. A particular form has a melting point of about 252° C. (DSC onset temperature). A specific form has a DSC peak at about 259° C. A specific form provides an XRPD pattern with peaks at one or more of about 4.4, 8.9, 12.8, and/or 16.1 degrees 2θ. Thus, one embodiment of the invention encompasses a crystalline edisilate salt of the compound having an XRPD pattern with peaks at about 4.4, 8.9, and 12.8 degrees 2θ.

Another embodiment of the invention encompasses crystalline esylate salts of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid. A particular form has a melting point of about 214° C. (DSC onset temperature). A specific form has a DSC peak at about 223° C. A specific form provides an XRPD pattern with peaks at one or more of about 8.1, 8.7, 13.0, 16.2, 18.3, and/or 20.2 degrees 2θ. Thus, one embodiment of the invention encompasses a crystalline esylate salt of the compound having an XRPD pattern with peaks at about 13.0, 16.2, and 18.3 degrees 2θ.

Another embodiment of the invention encompasses crystalline isopropyl sulfate salts of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid. A particular form has a melting point of about 194° C. (DSC onset temperature). A specific form has a DSC peak at about 204° C. A specific form provides an XRPD pattern with peaks at one or more of about 7.8, 15.6, 19.6, 23.6, and/or 31.6 degrees 2θ. Thus, one embodiment of the invention encompasses a crystalline isopropyl sulfate salt of the compound having an XRPD pattern with peaks at about 7.8, 15.6, and 19.6 degrees 2θ.

This invention encompasses solids that are mixtures of both amorphous and crystalline forms. Certain such solids comprise crystalline (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid or a pharmaceutically salt thereof in an amount of at least about 50, 75, 80, 85, 90, 95 or 99 weight percent.

(S)-2-Amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid can be prepared from methods described herein and known in the art. See, e.g., U.S. Pat. Nos. 7,553,840 and 7,709,493. Crystalline salts of the compound can be prepared by heating a solution comprising the compound and a pharmaceutically acceptable acid, reducing the solubility of the resulting salt, and isolating the crystalline salt.

5.3. Methods of Treatment

This invention encompasses a method of inhibiting tryptophan hydroxylase (TPH), which comprises contacting TPH with a compound of the invention (i.e., a compound disclosed herein).

This invention encompasses methods of treating, preventing, and managing various diseases and disorders mediated by peripheral serotonin, which comprise inhibiting TPH (e.g., the TPH1 isoform) activity in a patient in need of such treatment, prevention or management.

Particular diseases and disorders include carcinoid syndrome and gastrointestinal diseases and disorders. Examples of specific diseases and disorders include abdominal pain (e.g., associated with medullary carcinoma of the thyroid), anxiety, carcinoid syndrome, celiac disease, constipation (e.g., constipation having an iatrogenic cause, and idiopathic constipation), depression, diabetes, diarrhea (e.g., bile acid diarrhea, enterotoxin-induced secretory diarrhea, diarrhea having an iatrogenic cause, idiopathic diarrhea (e.g., idiopathic secretory diarrhea), and traveler's diarrhea), emesis, functional abdominal pain, functional dyspepsia, irritable bowel disease (IBD, including Crohn's disease and ulcerative colitis), irritable bowel syndrome (IBS), lactose intolerance, MEN types I and II, Ogilvie's syndrome, Pancreatic Cholera Syndrome, pancreatic insufficiency, pheochromacytoma, scleroderma, somatization disorder, and Zollinger-Ellison Syndrome.

Other diseases and disorders include cardiovascular and pulmonary diseases and disorders, such as acute and chronic hypertension, chronic obstructive pulmonary disease (COPD), pulmonary embolism (e.g., bronchoconstriction and pulmonary hypertension following pulmonary embolism), pulmonary hypertension (e.g., pulmonary hypertension associated with portal hypertension), and radiation pneumonitis (including that giving rise to or contributing to pulmonary hypertension). Others include abdominal migraine, adult respiratory distress syndrome (ARDS), carcinoid crisis, CREST syndrome (calcinosis, Raynaud's phenomenon, esophageal dysfunction, sclerodactyl), telangiectasia), Gilbert's syndrome, nausea, serotonin syndrome, subarachnoid hemorrhage, and ulcerative colitis. Still others include functional anorectal disorders, functional bloating, and functional gallbladder and sphincter of Oddi disorders.

5.4. Pharmaceutical Compositions

This invention encompasses pharmaceutical compositions and dosage forms comprising solid form of the invention. Pharmaceutical compositions and dosage forms of this invention may optionally contain one or more pharmaceutically acceptable carriers or excipients. Certain pharmaceutical compositions are single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration may require enteric coatings to protect the active ingredient from degradation within the gastrointestinal tract. In another example, the active ingredient may be administered in a liposomal formulation to shield it from degradative enzymes, facilitate transport in circulatory system, and/or effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18*th* ed., Mack Publishing, Easton Pa. (1990).

6. EXAMPLES

Some specific embodiments of the invention are described in the following examples.

6.1. Preparation of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl) propanoic acid 1-(4-Chloro-2-iodo-phenyl)-2,2,2-trifluoro-ethanol (0.840 g, 2.5 mmol), 3-methyl pyrazole (0.230 g, 2.8 mmol), CuI (0.190 g, 1.0 mmol), $K_2CO_3$ (0.863 g, 6.25 mmol), (1R, 2R)—N,N'-dimethyl-cyclohexane-1,2-diamine (0.071 g, 0.5 mmol) and toluene (10 ml) were combined in a 20 ml pressure tube, and the mixture was heated at 130° C. (oil bath temperature) for 12 hours. The mixture was diluted with ethyl acetate and washed with $H_2O$ (2×20 ml), brine, and dried over sodium sulfate. Removal of solvent gave a crude product, which was purified by ISCO column chromatography using 5-10% ethyl acetate in hexane as solvent to afford 1-[4-chloro-2-(3-methyl-pyrazol-1-yl)-phenyl]-2,2,2-trifluoro-ethanol (240 mg).

1-[4-Chloro-2-(3-methyl-pyrazol-1-yl)-phenyl]-2,2,2-trifluoro-ethanol (0.120 g, 0.41 mmol), (S)-3-[4-(2-amino-6-chloro-pyrimidine-4-yl)-phenyl]-2-tert-butoxycarbonylamino-propionic acid (0.176 g, 0.45 mmol), 1,4-dioxane (4 ml), and $Cs_2CO_3$ (0.533 g, 1.64 mmol) were combined in a 20 ml sealed tube, and the mixture was heated at 100° C. for 12 hours. The mixture was concentrated. To the residue, 10% methanol in DCM (50 ml) was added and the mixture was filtered. The filtrate was concentrated to give a crude product, which was taken in THF/3N HCl (30 ml/15 ml) and the resulting mixture was stirred at 40-45° C. for 12 hours. LCMS indicated the completion of reaction with desired product. The mixture was concentrated to give a crude product, which was dissolved in MeOH and $H_2O$ (1:1) and purified by preparative HPLC using MeOH/$H_2O$/TFA as solvent system to give (S)-2-amino-3-[4-(2-amino-6-{1-[4-chloro-2-(3-methyl-pyrazol-1-yl)-phenyl]-2,2,2-trifluoro-ethoxy}-pyrimidine-4-yl)-phenyl]-propionic acid as a TFA salt. LCMS: M+1=547. $^1$H-NMR (400 MHz, $CD_3OD$): δ (ppm) 2.30 (s, 3H), 3.10-3.30 (m, 2H), 4.20 (t, 1H), 6.32 (d, 1H), 6.74 (s, 1H), 7.0 (q, 1H), 7.38 (d, 2H), 7.50 (m, 2H), 7.72 (m, 1H), 7.90 (m, 3H).

6.2. Preparation of Crystalline (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl) phenyl)propanoic acid Crystalline free-base (neutral form) was obtained by mixing amorphous (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid (101.2 mg) with 1 ml MeCN/$H_2O$. The resulting suspension was shaken with an Eppendorf Thermomixer for five days using the following temperature program: four hours at 20° C., heating to 40° C. in two hours, two hours at 40° C., cooling to 20° C. in four hours. The resulting solid was filtered off to afford crystalline needles.

6.3. Preparation of Crystalline (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl) phenyl)propanoic acid Besylate To a 500 L glass lined reactor was charged (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl) propanoic acid (76.4 kg methyl THF solution, 12 kg assay adjusted). The solution was concentrated to 34-38 L at below 55° C. under −0.06-0.07 Mpa. More 2-methyl THF (102 kg) was added and the water content of the solution was found to be 5%. The solution was concentrated to 56-65 L at below 55° C. under −0.06 to −0.07 Mpa. The batch was heated to 50-55° C. and 67 kg of 2-methyl THF was added slowly through a pipe filtered at 50-55° C. over 30 minutes. (S)-2-amino-3-(4-(2-amino-6-((R)-1-(4-chloro-2-(3-methyl-1H-pyrazol-1-yl) phenyl)-2,2,2-trifluoroethoxy)pyrimidin-4-yl)phenyl)propanoic acid seed (60 g) in a small amount of 2-methyl THF was added into the reactor and the mixture was stirred at 50-55° C. over 1 hour. Additional 2-methyl THF (77 kg) was added at 50-55° C. through a pipe filter in 2 hours and the mixture was stirred for 2 hours at the same temperature before being concentrated to 78-90 L at below 55° C. under −0.06 to −0.07 Mpa.

After concentration, the volume of the mixture was adjusted by adding 51 kg of methyl THF at 50-55° C. The mixture was stirred at 50-55° C. for 2 hours and then cooled to 20-25° C. and stirred for 10 hours. The solid was filtered through a centrifuge. The reactor and the centrifuge were washed with 2-methyl THF twice (2×30 kg). The wet cake of free base was dried at 50-60° C. under vacuum for 10 hours. The free base was charged into a 300 L glass lined reactor containing 13 kg benzenesulfonic acid in acetonitrile solution (prepared by adding 3.45 kg benzenesulfonic acid hydrate (assay 87.1%, assay adjusted weight 3.00 kg) in 32 kg of acetonitrile), 7.5 kg of acetic acid and 7 kg of acetonitrile. The mixture was heated to 58-63° C. and stirred for 2.5 hours until all solid was dissolved. Additional 4.9 kg of benzenesulfonic acid acetonitrile solution was added and the mixture was stirred at 58-63° C. for 10-15 minutes. (S)-2-amino-3-(4-(2-amino-6-((R)-1-(4-chloro-2-(3-methyl-1H-pyrazol-1-yl) phenyl)-2,2,2-trifluoroethoxy)pyrimidin-4-yl)phenyl)propanoic acid besylate seed (45 g) was added and the mixture was stirred for 2 hours. The final portion of benzenesulfonic acid acetonitrile solution (16.8 kg) was slowly added in 2 hours and the mixture was stirred at 58-63° C. for 1 hour.

The containers of the benzenesulfonic acid acetonitrile solution was rinsed with 32 kg of acetonitrile and the rinse was slowly added into the reactor in 2 hours. The slurry was stirred at 58-63° C. for 3 hours before slowly cooled to 20-25° C. in 2-4 hours. The slurry was stirred at 20-25° C. for 12 hours and then filtered with a centrifuge. The reactor and the wet cake were washed with acetonitrile three times (3×20 kg). The wet cake (15.44 kg) was dried at 50-60° C. under vacuum for 40 hours. The product (besylate Form C), was unloaded and sieved. Yield 11.46 kg, assay 99.3%, assay adjusted yield 74%, purity 99.6%.

6.4. Preparation of Crystalline (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl) phenyl)propanoic acid Dibesylate To the solution of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid free base (3.66 mL, 0.05 M, 0.183 mmol) in MeOH was added 1.0N benzenesulfonic acid (0.56 mL, 3.0 equiv.) prepared from IPA. After the solvent was evaporated, 3.0 mL IPA was added to give a clear solution. After adding 4.0 mL heptane in the period of 5 min, the reaction mixture was stirred for 2 hours. The solid was filtered, washed with, dried overnight under vacuum at 45° C. to give 135 mg (85.5% yield) (S)-2-amino- 3-(4-(2-amino-6-((R)-1-(4-chloro-2-(3-methyl-1H-pyrazol-1-yl)phenyl)-2,2,2-trifluoroethoxy)pyrimidin-4-yl)phenyl) propanoic acid dibesylate as an off-white solid.

The crystallinity of the solid was confirmed by XRPD. The DSC exhibited a sharp peak at 226.8° C. TGA showed about 15% weight loss up to 240° C., and an additional 27.5% weight loss up to 350° C. Scanning electron microscopy (SEM) imaging of the solid showed rod-like crystals.

6.5. Preparation of Crystalline (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl) phenyl)propanoic acid Edisilate A flask was charged with 0.5 mL of (S)-2-amino-3-(4-(2-amino-6-((R)-1-(4-chloro-2-(3-methyl-1H-pyrazol-1-yl) phenyl)-2,2,2-trifluoroethoxy)pyrimidin-4-yl)phenyl)propanoic acid free base (0.05 M, 0.025 mmol) in MeOH and 0.28 mL ethane-1,2-disulfonic acid in IPA (0.1N, 0.028 mmol, 1.1 equiv.). After the solvent was evaporated, 0.5 mL of ethanol/H$_2$O (100:5) was added. The white suspension was heated to 75° C. and stirred until the solid was completely dissolved (about 15 minutes). After stirred overnight at room temperature, the solid was filtered, washed with 0.5 mL heptane, and dried at 45° C. under vacuum overnight to afford (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid edisilate (12.5 mg, 68% yield) as off-white solid.

The crystallinity of the solid was confirmed by XRPD. The DSC exhibited a sharp peak at 258.5° C. TGA showed about 0.95% weight loss up to about 120° C., and 16.2% up to about 250° C. SEM imaging of the solid showed plane-like crystals.

6.6. Preparation of Crystalline (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl) phenyl)propanoic acid Esylate A flask was charged with 0.5 mL of (S)-2-amino-3-(4-(2-amino-6-((R)-1-(4-chloro-2-(3-methyl-1H-pyrazol-1-yl) phenyl)-2,2,2-trifluoroethoxy)pyrimidin-4-yl)phenyl)propanoic acid free base (0.05 M, 0.025 mmol) in MeOH, and 0.28 mL ethanesulfonic acid in IPA (0.1N, 0.028 mmol, 1.1 equiv.). After the solvent was evaporated, 0.75 mL MeCN was added and stirred to give a suspension, followed by adding 0.2 mL EtOH and heated until the solid was completely dissolved. After stirring overnight, the crystal was filtered off, washed with heptane (0.6 mL), dried at 45° C. under vacuum to give (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid esylate (69% yield).

The crystallinity of the solid was confirmed by XRPD. The DSC exhibited a sharp peak at 222.8° C. TGA showed 41.7% weight loss up to about 390° C.; the combustion of the ethanesulfonic acid produced 16% weight loss up to 570° C. SEM imaging of the solid showed needle-like crystals.

6.7. Preparation of Crystalline (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl) phenyl)propanoic acid Isopropyl Sulfate 1.0N isopropyl sulfuric acid (0.19 mL, 1.04 eq) in IPA was added to a solution of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid free base (3.66 mL, 0.05M, 0.183 mmol) in MeOH and followed by evaporation of solvent to dry. After adding of 6.5 mL MeCN/IPA (3/1) and heating at 75° C., a clear solution was obtained. 2.0 mL solvent was evaporated and stirred overnight. The precipitate was collected by filtration. The cake was washed with heptane, dried at 45° C. under vacuum overnight to give 68 mg (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid isopropyl sulfate, (54% yield).

The crystallinity of the solid was confirmed by XRPD. The DSC exhibited a sharp peak at 203.98° C. TGA showed about 1.3% weight loss up to about 200° C. SEM imaging of the solid showed rod-like crystals.

All references (e.g., patents and patent applications) cited above are incorporated herein by reference in their entireties.

What is claimed is:

1. A crystalline compound, which is (S)-2-amino-3-(4-(2-amino-6-((R)-1-(4-chloro-2-(3-methyl-1H-pyrazol-1-yl) phenyl)-2,2,2-trifluoroethoxy)pyrimidin-4-yl)phenyl)propanoic acid besylate.

2. The crystalline compound of claim 1, which is anhydrous.

3. The crystalline compound of claim 2, which has a melting point of about 234° C. and/or a DSC peak at about 238° C.

4. The crystalline compound of claim 3, which has an X-ray powder diffraction pattern comprising a peak at one or more of about 9.2, 15.9, 16.8, 18.4, 19.8, and/or 20.8 degrees 2θ.

5. The crystalline compound of claim 1, which is a hydrate.

6. The crystalline compound of claim 5, which has a melting point of about 218° C.

7. The compound of claim 5, which has an X-ray powder diffraction pattern comprising a peak at one or more of about 8.7, 9.1, 13.4, 18.3, and/or 20.2 degrees 2θ.

8. The crystalline compound of claim 2, which has a melting point of about 228° C. and/or a DSC peak at about 233° C.

9. The crystalline compound of claim 2, which has an X-ray powder diffraction pattern comprising a peak at one or more of about 8.7, 9.5, 16.9, 17.5, 19.1, 19.7, 20.1, 20.4, 21.8, 22.1, and/or 26.4 degrees 2θ.

10. The crystalline compound of claim 2, which has an X-ray powder diffraction pattern substantially the same as that shown in FIG. 1.

11. The crystalline compound of claim 3, which has an X-ray powder diffraction pattern comprising a peak at one or more of about 7.6, 8.6, 12.9, 15.0, 15.3, 17.3, 19.2, 19.5, 20.2, and/or 23.1 degrees 2θ.

12. A pharmaceutical dosage form comprising the crystalline compound of claim 1.

* * * * *